(12) United States Patent
Feler et al.

(10) Patent No.: US 11,607,539 B2
(45) Date of Patent: Mar. 21, 2023

(54) PADDLE LEADS FOR NEUROSTIMULATION AND METHOD OF DELIVERING THE SAME

(71) Applicant: Advanced Neuromodulation Systems, Inc., Plano, TX (US)

(72) Inventors: Joshua R. Feler, Carbondale, CO (US); Claudio A. Feler, Carbondale, CO (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 459 days.

(21) Appl. No.: 16/565,178

(22) Filed: Sep. 9, 2019

(65) Prior Publication Data

US 2020/0016397 A1 Jan. 16, 2020

Related U.S. Application Data

(63) Continuation of application No. 14/198,260, filed on Mar. 5, 2014, now abandoned.

(60) Provisional application No. 61/791,288, filed on Mar. 15, 2013.

(51) Int. Cl.
*A61N 1/05* (2006.01)

(52) U.S. Cl.
CPC .................. *A61N 1/0553* (2013.01)

(58) Field of Classification Search
CPC ............... A61N 1/0551; A61N 1/0053; A61N 2001/058; A61N 1/0558; A61N 1/3605–3611; A61B 1/0551
See application file for complete search history.

(56) References Cited

U.S. PATENT DOCUMENTS

| | | | |
|---|---|---|---|
| 7,697,995 B2* | 4/2010 | Cross, Jr. ............. | A61N 1/0553 607/117 |
| 8,224,459 B1* | 7/2012 | Pianca ................. | A61N 1/0553 607/117 |
| 2012/0029528 A1* | 2/2012 | MacDonald ......... | A61N 1/0553 606/129 |

* cited by examiner

*Primary Examiner* — Majid Jamialahmadi
(74) *Attorney, Agent, or Firm* — The Small Patent Law Group LLC; Dean D. Small (57) ABSTRACT

Paddle lead including a lead body having a distal end, a proximal end, and a central axis extending therebetween. The lead body includes opposite first and second sides that extend between the distal and proximal ends. The paddle lead also includes electrodes disposed along the first side of the lead body that are configured to apply neurostimulation therapy within an epidural space of a patient. The electrodes are electrically coupled to conductive pathways that extend through the proximal end of the lead body. The lead body includes a flexible material a flexible material that is configured to flex when a fluid pressure is imposed on the lead body in the epidural space. The lead body is configured to have a non-planar contour that folds or curves about the central axis when experiencing the fluid pressure.

12 Claims, 7 Drawing Sheets

PADDLE LEADS FOR NEUROSTIMULATION AND METHOD OF DELIVERING THE SAME

CROSS-REFERENCE TO RELATED APPLICATION

This application is a continuation of U.S. application Ser. No. 14/198,260, filed Mar. 5, 2014, which is incorporated herein by reference in its entirety. The present application claims the benefit of U.S. Provisional Application No. 61/791,288, filed on Mar. 15, 2013, which is incorporated herein by reference in its entirety.

FIELD OF THE INVENTION

One or more embodiments of the subject matter described herein generally relate to systems having paddle leads for generating electric fields proximate to nerve tissue.

BACKGROUND

Neurostimulation systems (NS) are devices that generate electrical pulses and deliver the pulses to nerve tissue to treat a variety of disorders. Spinal cord stimulation (SCS) is a common type of neurostimulation. In SCS, electrical pulses are delivered to nerve tissue in the spine typically for the purpose of chronic pain control. While a precise understanding of the interaction between the applied electrical energy and the nerve tissue is not fully appreciated, it is known that application of an electric field to spinal nerve tissue can effectively mask or alleviate certain types of pain transmitted from regions of the body associated with the stimulated nerve tissue.

NS and SCS systems generally include a pulse generator and one or more leads electrically coupled to the pulse generator. A lead includes an elongated body of insulative material. A stimulating end portion of the lead includes multiple electrodes that are electrically coupled to the pulse generator through wire conductors. The stimulating end portion of a lead is implanted proximate to nerve tissue (e.g., within epidural space of a spinal cord) to deliver the electrical pulses. A proximal end of the lead body includes multiple terminal contacts, which are also electrically coupled to the wire conductors. The terminal contacts, in turn, are electrically coupled to the pulse generator. The terminal contacts receive electrical pulses from the pulse generator that are then delivered to the electrodes through the wire conductors to generate the electric fields. The pulse generator is typically implanted within the individual and may be programmed (and re-programmed) to provide the electrical pulses in accordance with a designated sequence.

Typically, one of two types of leads is used. The first type is a percutaneous lead, which has a rod-like shape and includes electrodes spaced apart from each other along a single axis. The second type of lead is a laminectomy or laminotomy lead (hereinafter referred to as a "paddle" lead). A paddle lead has an elongated planar body with a thin rectangular shape (i.e., paddle-like). Although the paddle lead may include only one row or column of electrodes, the paddle lead typically includes an array of electrodes that are spaced apart from each other along a substantially common plane. The number of electrodes may be, for example, two, four, eight, or sixteen. Due to their dimensions and physical characteristics, conventional paddle leads require a surgical procedure (a partial laminectomy) to implant the lead. The lead is typically positioned within the epidural space adjacent to the dura of the spinal cord.

However, conventional paddle leads include a rigid, substantially inflexible body. In some cases, the dimensions of the epidural space and the dimensions of the paddle lead result in the paddle lead pressing against the spinal cord. If the compression is substantial, it may cause unwanted consequences, such as a tingling sensation, pain, partial paralysis, or even complete paralysis of the legs.

Therefore, a need remains for implantable paddle leads that do not compress the nerves of the spinal cord or compress the nerves less than known paddle leads.

BRIEF SUMMARY

In accordance with an embodiment, a neurostimulating paddle lead is provided that includes a lead body having a distal end, a proximal end, and a central axis extending therebetween. The lead body includes opposite first and second sides that extend between the distal and proximal ends. The paddle lead also includes electrodes disposed along the first side of the lead body that are configured to apply neurostimulation therapy within an epidural space of a patient. The electrodes are electrically coupled to conductive pathways that extend through the proximal end of the lead body. The lead body includes a flexible material a flexible material that is configured to flex when a fluid pressure is imposed on the lead body in the epidural space. The lead body is configured to have a non-planar contour that folds or curves about the central axis.

The lead body may have longitudinal edges that join the first and second sides. The longitudinal edges may extend generally along the central axis. The longitudinal edges may close around a dura membrane when experiencing the fluid pressure. For example, the lead body may be configured to flex such that the longitudinal edges move closer to each other within the epidural space. As another example, the central axis may extend along a geometric center of a cross-section of the lead body that is transverse to the central axis. In some embodiments, the longitudinal edges and the central axis do not exist within a common plane when the leady body is in the epidural space.

In some embodiments, the lead body is configured to flex within the epidural space when the fluid pressure is at least 15 cmH$_2$O. In some embodiments, the lead body is configured to flex within the epidural when the fluid pressure is at least 5 cmH$_2$O.

The paddle lead may also include a tool receptacle that is coupled to the lead body along the second side. The tool receptacle may have a receptacle cavity that opens along the second side or the proximal end. In some instances, the lead body and the tool receptacle may be integrally formed, such as through a common molding process.

In another embodiment, a lead-delivery assembly is provided that includes a paddle lead having a distal end, a proximal end, and a central axis extending therebetween. The paddle lead includes opposite first and second sides that extend between the distal and proximal ends. The paddle lead includes electrodes that are disposed along the first side of the paddle lead and that are configured to apply neurostimulation therapy within an epidural space of a patient. The lead-delivery assembly also includes a tool receptacle that is coupled to the paddle lead. The tool receptacle may have a receptacle cavity that opens along the second side or along the proximal end. The lead-delivery assembly may also include a delivery tool having a leading end. The leading end is sized and shaped for insertion into the receptacle cavity.

In some embodiments, the tool receptacle is integrally formed with the paddle lead. In some aspects, the cavity is a lumina having an opening along the second side. The lumina may extend from the opening toward the distal end.

The tool receptacle may include a pocket having the cavity. The cavity of the pocket may have a width that is greater than half of a width of the lead body. The delivery tool may have a leading edge with a greatest dimension that extends along the width of the cavity when the delivery tool is disposed within the cavity.

In another embodiment, a lead-delivery assembly is provided that includes a paddle lead having a distal end, a proximal end, and a central axis extending therebetween. The paddle lead includes opposite first and second sides that extend between the distal and proximal ends. The paddle lead includes electrodes that are disposed along the first side of the paddle lead and are configured to apply neurostimulation therapy within an epidural space of a patient. The lead-delivery assembly includes an insert tray configured to removably hold the paddle lead. The insert tray has a planar body with an open-sided recess that is dimensioned to hold the paddle lead. The lead-delivery assembly also includes a delivery tool having a leading end. The leading end is configured to engage the insert tray to position the paddle lead within the epidural space. In some aspects, the insert tray may have a distal shroud that is configured to surround the distal end of the paddle lead.

In another embodiment, a method of locating a paddle lead in an epidural space of a patient is provided. The method includes inserting a delivery tool into a tool receptacle of a paddle lead. The paddle lead has opposite first and second sides that extend between distal and proximal ends of the paddle lead. The paddle lead includes electrodes that are disposed along the first side. The tool receptacle is disposed along the second side. The method also includes directing the paddle lead into an epidural space of a patient and to a designated location in the epidural space and removing the delivery tool from the tool receptacle.

In some aspects, the tool receptacle is integrally formed with the paddle lead. The cavity may be a lumina having an opening along the second side. The lumina may extend from the opening toward the distal end. The tool receptacle includes a pocket having the cavity. The cavity of the pocket has a width that is greater than half of a width of the lead body. The delivery tool has a leading edge with a greatest dimension that extends along the width of the cavity when the delivery tool is disposed within the cavity.

In another embodiment, a method of locating a paddle lead in an epidural space of a patient is provided. The method includes positioning a paddle lead on an insert tray that is configured to removably hold the paddle lead. The insert tray has a planar body with an open-sided recess that is dimensioned to hold the paddle lead. The method also includes directing the insert tray into an epidural space of a patient and to a designated location in the epidural space and removing the insert tray from the paddle lead.

The insert tray may include a distal shroud that is configured to surround the distal end of the paddle lead. In some embodiments, directing the insert tray into the epidural space includes using a delivery tool to direct the insert tray.

While multiple embodiments are disclosed, still other embodiments of the described subject matter will become apparent to those skilled in the art from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

DETAILED DESCRIPTION

Figure 1:
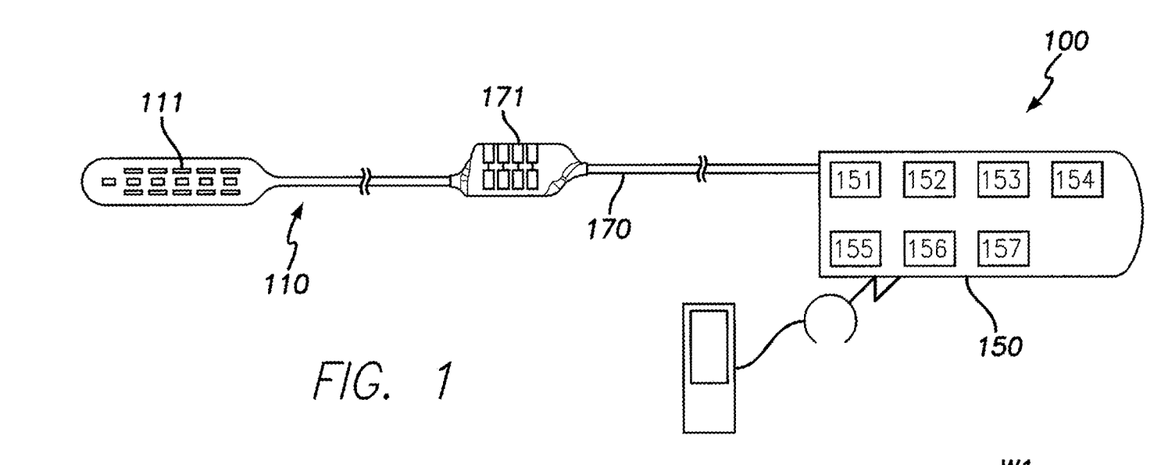
FIG. 1 is a schematic view of one embodiment of a neurostimulating (NS) system in accordance with one embodiment.

Embodiments described herein include paddle leads that are capable of conforming in shape after the paddle lead is inserted into the epidural space. For example, the paddle lead may be configured to flex or bow along the width and/or length when a fluid pressure in the dura is imposed on the lead body in the epidural space. In some cases, the flexible paddle lead may prevent or reduce pressure along the spinal nerves. FIG. 1 depicts a neurostimulation (NS) system 100 that generates electrical pulses for application to tissue, such as spinal cord tissue, of a patient according to one embodiment. For embodiments that stimulate spinal cord tissue, the nerve tissue may include dorsal column (DC) fibers and/or dorsal root (DR) fibers. The NS system 100 includes an NS device (or pulse generator) 150 that is adapted to generate electrical pulses in order to apply electric fields to the tissue. The NS device 150 is typically implantable within an individual (e.g., patient) and, as such, may be referred to as an implantable pulse generator (IPG). The implantable NS device 150 typically comprises a housing that encloses a controller 151, a pulse generating circuitry 152, a charging coil 153, a battery 154, a far-field and/or near field communication circuitry 155, a battery charging circuitry 156, a switching circuitry 157, etc. of the device. The controller 151 typically includes a processor or other logic-based device for controlling the various other components of the NS device 150. Software code is typically stored in memory of the NS device 150 for execution by the processor to control the various components of the device.

The NS device 150 may comprise a separate or an attached extension component 170. If the extension component 170 is a separate component, the extension component 170 may connect with the "header" portion of the NS device 150 as is known in the art. If the extension component 170 is integrated with the NS device 150, internal electrical connections may be made through respective conductive components. Within the NS device 150, electrical pulses are generated by the pulse generating circuitry 152 and are provided to the switching circuitry 157. The switching circuitry 157 connects to outputs of the NS device 150. Electrical connectors (e.g., "Bal-Seal" connectors) within a connector portion 171 of the extension component 170 or within the header may be employed to conduct the electrical pulses. Terminal contacts (not shown) of one or more neurostimulator leads 110 are inserted within the connector portion 171 or within the header for electrical connection with respective connectors. Thereby, the pulses originating from NS device 150 are provided to the neurostimulator lead 110. The pulses are then conducted through wire conductors of the lead 110 and applied to tissue of an individual via electrodes 111. In the illustrated embodiment, the neurostimulator lead is a lead configured for insertion after a laminectomy or a laminotomy. The lead is hereinafter referred to as a "paddle lead."

For implementation of the components within NS device 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference. One or more NS device and one or more paddle leads that may be used with embodiments described herein are described in U.S. Patent Application Publication No. US 2013/0006341.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within the NS device 150. Different pulses on different electrodes may be generated using a single set of pulse generating circuitry using consecutively generated pulses according to a "multi-stimset program." Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Figure 2:
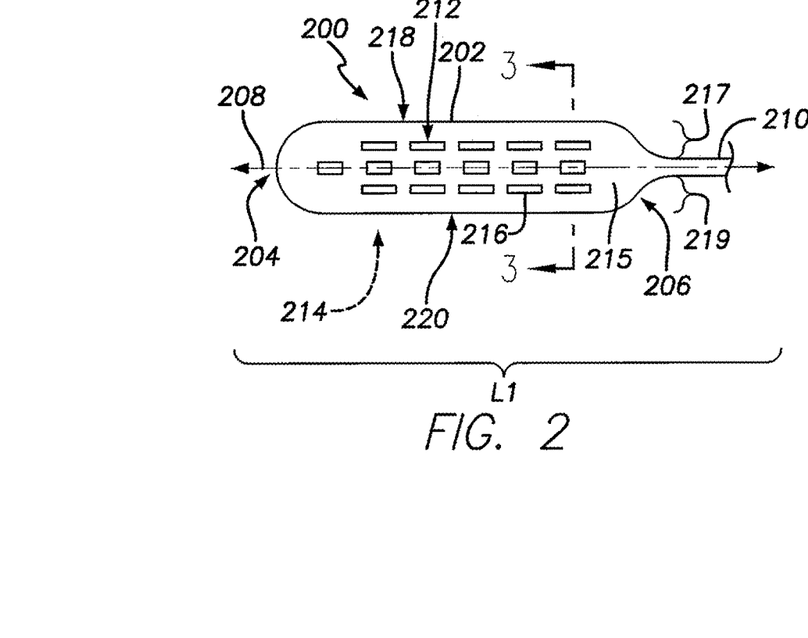
FIG. 2 is a plan view of a paddle lead formed in accordance with one embodiment that may be used with the NS system of FIG. 1.
Figure 3:
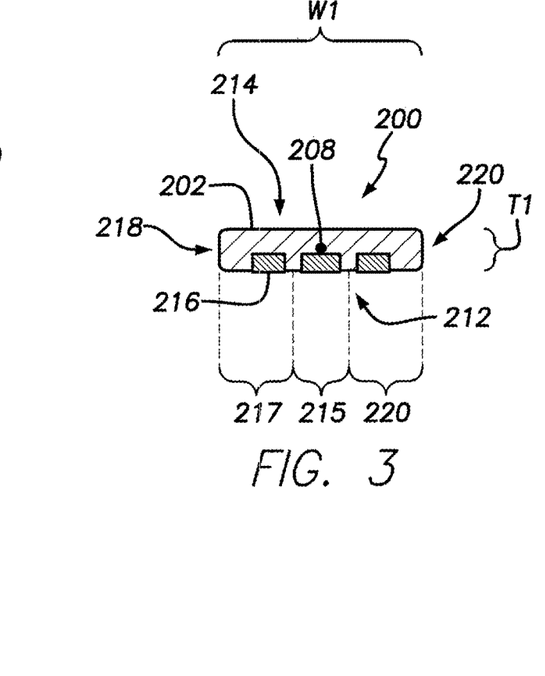
FIG. 3 is a cross-section of the paddle lead of FIG. 2 taken along the line 3-3 in FIG. 2.

FIGS. 2 and 3 illustrate a plan view and a cross-section, respectively, of a paddle lead 200 formed in accordance with one embodiment. The paddle lead 200 includes a lead body 202 having a distal end 204 (FIG. 2), a proximal end 206 (FIG. 2), and a central axis 208 extending therebetween. As shown in FIG. 3, the central axis 208 extends generally along a geometric center of a cross-section of the paddle lead 200.

During an implantation procedure, the distal end 204 is typically the leading end that is inserted through an incision and into the spinal column. As shown, a cable or tube 210 extends from the proximal end 206. The cable 210 may include conductive pathways (e.g., wire conductors) that extend from the lead body 202 to an NS device or pulse generator (not shown), such as the NS device 150 (FIG. 1). The lead body 202 also includes opposite first and second sides 212 and 214 that extend between the distal and proximal ends 204, 206.

The paddle lead 200 also includes longitudinal edges 218, 220 that extend along a length (e.g., a greatest dimension) of the lead body 202. The longitudinal edges 218, 220 may extend generally along or parallel to the central axis 208. As shown in FIG. 3, the longitudinal edges 218, 220 may also join the first and second sides 212, 214.

The paddle lead 200 may be characterized as having a central portion 215 that includes the central axis 208 and extends between the first and second sides 212, 214 and first and second wing portions 217, 219. The first and second wing portions 217, 219 are joined by the central portion 215 and extend to the longitudinal edges 218, 220, respectively.

The lead body 202 has a length IA that extends along the central axis 208 between the distal and proximal ends 204, 206, a width W1 that extends transverse to the central axis 208 between the longitudinal edges 218, 220, and a thickness T1 that extends between the first and second sides 212, 214. Although the thickness $T_1$ is shown as being substantially uniform, in other embodiments, the thickness $T_1$ may vary. For example, the central portion 215 may have a greater thickness than the wing portions 217, 219. For some portions of the lead body 202, the thickness $T_1$ may change abruptly or more gradually as the thickness T1 extends along the width $W_1$ or along the length $L_1$. For instance, the thickness $T_1$ may reduce or taper as the wing portion 217, 219 approach the longitudinal edges 218, 220.

The paddle lead 200 also includes a plurality of electrodes 216 that are disposed along the first side 212 and are configured to provide a neurostimulation therapy in an epidural space of a patient. For example, electrical pulses transmitted from the pulse generator may be provided at a predetermined schedule or frequency to provide an effective therapy for the patient. The second side 214, when the paddle lead is disposed in the epidural space, may interface with an anatomical structure (e.g., bone, ligament, or other portions of the spine). As described herein, the paddle lead 200 may be configured to change or conform the contour of the lead body 202.

Figures 4, 5:
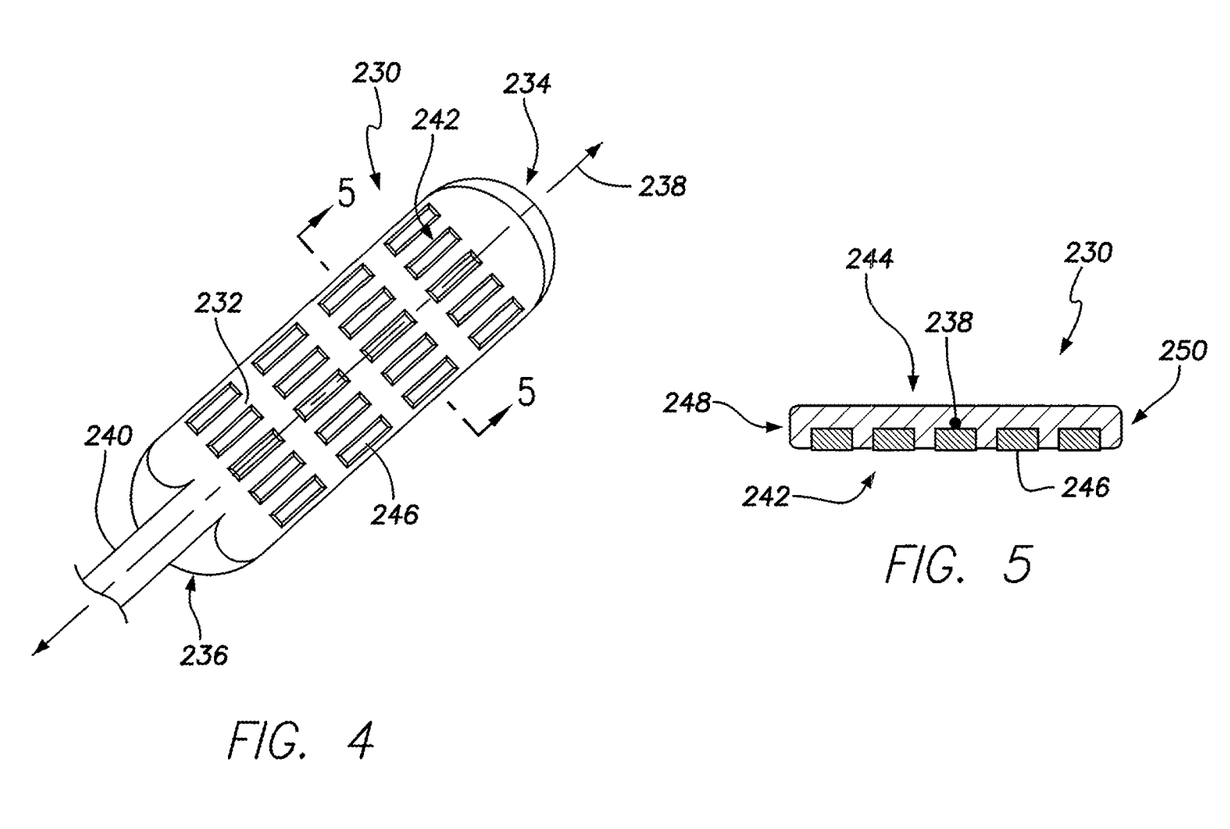
FIG. 4 is an isolated view of a paddle lead formed in accordance with one embodiment that may be used with the NS system of FIG. 1.
FIG. 5 is a cross-section of the paddle lead of FIG. 4 taken along the line 5-5 in FIG. 4.

FIGS. 4 and 5 illustrate an isolated view and a cross-section, respectively, of a paddle lead 230 formed in accordance with one embodiment. The paddle lead 230 includes a lead body 232 having a distal end 234 (FIG. 2), a proximal end 236 (FIG. 2), and a central axis 238 extending therebetween. As shown in FIG. 5, the central axis 238 extends generally along a geometric center of a cross-section of the paddle lead 230.

Like the paddle lead 200 (FIG. 2), the paddle lead 230 includes a cable or tube 240 that extends from the proximal end 236. The cable 240 includes conductive pathways (e.g., wires) that extend from the lead body 232 to a pulse generator (not shown). The lead body 232 also includes opposite first and second sides 242 and 244 that extend between the distal and proximal ends 234, 236. The paddle lead 230 also includes longitudinal edges 248, 250 that extend along a length (e.g., a greatest dimension) of the lead body 232. The longitudinal edges 248, 250 may extend generally along or parallel to the central axis 238. As shown in FIG. 5, the longitudinal edges 248, 250 may also join the first and second sides 242, 244.

The paddle lead 230 also includes a plurality of electrodes 246 that are disposed along the first side 242 and are configured to provide neurostimulation therapy in an epidural space of a patient. In the illustrated embodiment, the electrodes 246 form an array that includes a 5×4 grid of electrodes 246 in which the electrodes 246 are substantially evenly distributed along the central axis 238. In alternative embodiments, the electrodes 246 may form a single row or column that extends along the central axis 238 and are spaced apart from each other. The second side 244, when the paddle lead is disposed in the epidural space, may interface with an anatomical structure (e.g., bone, ligament, or other portions of the spinal column. Although not indicated, the lead body 232 may have a central portion and first and second wing portions like the lead body 202. Of course, the lead body 232 also has a length, width, and thickness.

In particular embodiments, the characteristics of the materials used to form the lead bodies 202, 232 and/or the dimensions (e.g., thickness) of the lead bodies 202, 232 permit the lead bodies 202, 232 to be readily flexible or conformable (e.g., supple) when a designated amount of fluid pressure provided through the dura is experienced. The lead body 202, 232 may include one or more biocompatible materials. The materials may be electrically insulating (e.g., dielectric materials). Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. In some embodiments, the material of the lead body that surrounds the metal components (e.g., electrodes and the wire conductors that couple to the electrodes) consists essentially of at least one of polyimide, polyetheretherketone (PEEK), polyethylene terephthalate (PET) film, polytetrafluoroethylene (PTFE), parylene, polyether bloc amides, or polyurethane.

In certain embodiments, the dimensions of the lead bodies 202, 232 are configured such that the lead bodies 202, 232 are flexible when a fluid pressure is imposed on the lead body in the epidural space. For example, the thickness for one or more portions of the lead body may not exceed a designated amount and/or the thickness for one or more designated portions of the lead body may be reduced to allow flexing. The lead bodies may also be characterized as being malleable, supple, conformable, and/or moldable.

By way of example, the fluid pressure imposed in the epidural space may be between about 5 to about 20 $cmH_2O$ (or about 4 to about 15 mmHg). Thus, embodiments may be configured to flex within the epidural space when the fluid pressure in the spinal canal is above at least 5 $cmH_2O$, 6 cmH2O, 7 cmH2O, 8 cmH2O, 9 cmH2O, 10 $cmH_2O$, 11 cmH2O, 12 $cmH_2O$, 13 cmH2O, 14 cmH2O, 15 cmH2O, 16 $cmH_2O$, 17 $cmH_2O$, 18 $cmH_2O$, 19 cmH2O, or 20 cmH2O. In some embodiments, the lead body is configured to flex within the epidural space when the fluid pressure is at least 5 $cmH_2O$. In particular embodiments, the leady body is configured to flex within the epidural space when the fluid pressure is at least 10 $cmH_2O$ or, more particularly, at least 15 cmH2O.

In some cases, one or more portions of the lead body may include more rigid structures or stiffeners. For example, the longitudinal edges may include a more rigid dielectric material that extends along the longitudinal edges for at least a portion of the length. The distal end may also include portions that have a more rigid material.

When the lead body of a paddle lead is flexed or shaped between the dura and another anatomical structure (e.g., ligamentum flavum), the shape of the lead body may change the effective arrangement of the electrodes with respect to each other. In some embodiments, the pattern or arrangement of the electrodes may be configured or re-arranged based on the operative shape of the lead body (or ranges of shapes that the lead body may change between). More specifically, the arrangement of electrodes may be customized for each patient. In some embodiments, the arrangement of electrodes may be based, at least in part, on data obtained regarding an anatomical configuration of a target location for the paddle lead (e.g., the location where the lead will be operating to provide neurostimulation). For example, the data may include images of the location where the paddle lead will be implanted. Accordingly, at least some of the arrays or patterns of electrodes may be irregular. For instance, one row (or column) of electrodes may have different separation distances between adjacent electrodes and an adjacent row (or column) may also have different separation distances between adjacent electrodes. The patterns for each of the rows (or columns) may be different.

As one example of differently patterned rows or columns, a first row or column may have five electrodes in which the first and second electrodes are separated by X, the second and third electrodes are separated by 1.05 X, the third and fourth electrodes are separated by 0.95 X, and the fourth and fifth electrodes are separated by 0.85 X. A second row or column may have five electrodes in which the first and second electrodes are separated by Y, the second and third electrodes are separated by 0.85 Y, the third and fourth electrodes are separated by 0.95 Y, and the fourth and fifth electrodes are separated by Y. In some embodiments, Y may equal X.

Figure 6:
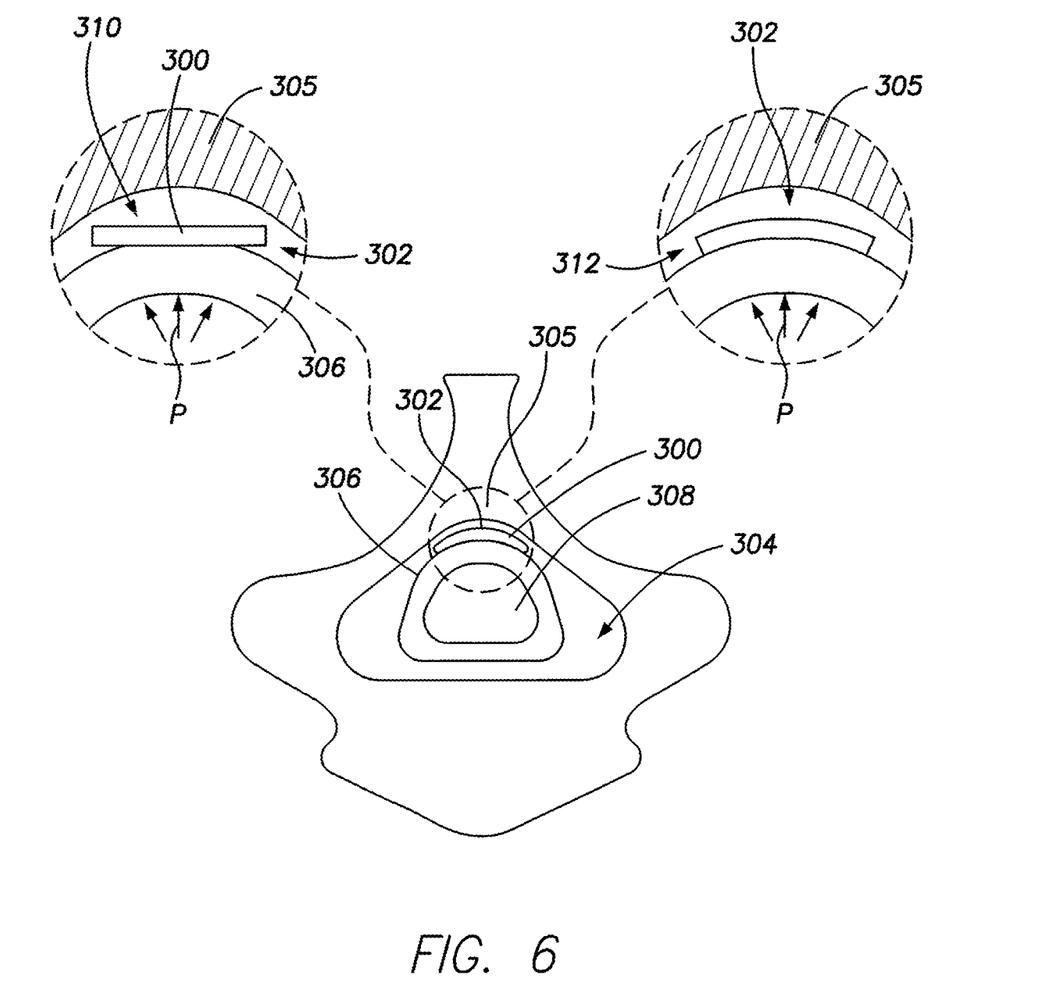
FIG. 6 is a view of a paddle lead formed in accordance with one embodiment located within an epidural space of a spinal canal of a patient.

FIG. 6 is a view of a paddle lead 300 that is located within an epidural space 302 of a spinal canal 304 of a patient. For reference, the dura membrane 306, the spinal cord 308, and the vertebra 305 are also shown. The paddle lead 300 may be similar or identical to the paddle leads 200 and 230 described with respect to FIGS. 2 and 3, respectively. Other paddle leads may also be used as set forth herein. FIG. 6 provides enlarged views in which the paddle lead has a pre-loaded shape or condition 310 and a loaded shape or condition 312. The pre-loaded shape 310 may be the shape of the paddle lead 300 before the fluid pressure is imposed on the paddle lead 300 in the epidural space 302.

The loaded shape 312 may be the shape of the paddle lead 300 when the paddle lead is operatively positioned at a designated location in the epidural space 302 and the fluid pressure causes the paddle lead to change shape. The fluid pressure is indicated by the arrows P in the enlarged views. In the loaded shape 312, the fluid pressure P, the dimensions of the epidural space 302 defined by various anatomical structures, and the dimensions and malleability of the paddle lead 300 may determine the configuration of the paddle lead 300 in the loaded shape 312. For example, the paddle lead 300 may conform to the anatomical structures in the surrounding environment, such as the vertebra 305, dura membrane 306, or other structures (e.g., ligaments, fat). In FIG. 6, the shape of the paddle lead 300 is primarily determined by the dura membrane 306.

Figure 7:
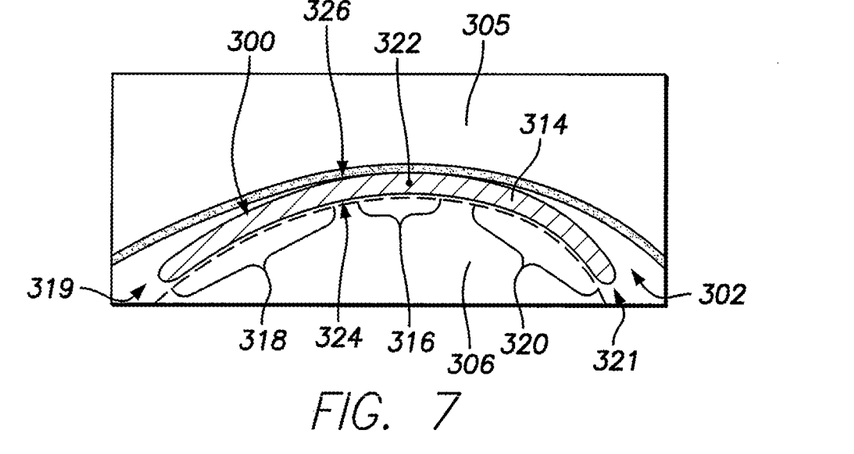
FIG. 7 is a cross-section of a paddle lead formed in accordance with one embodiment that is configured to flex about a central axis when experiencing a fluid pressure from a dura membrane.
Figure 8:
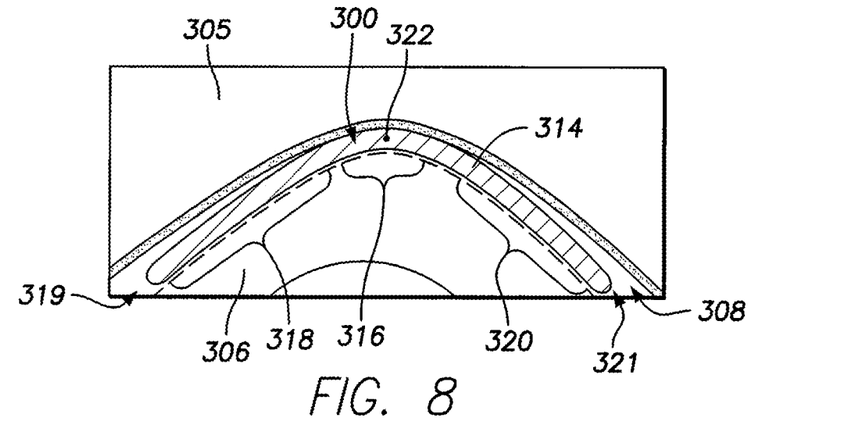
FIG. 8 is another cross-section of a paddle lead formed in accordance with one embodiment that is configured to flex about a central axis when experiencing a fluid pressure from a dura membrane.
Figure 9:
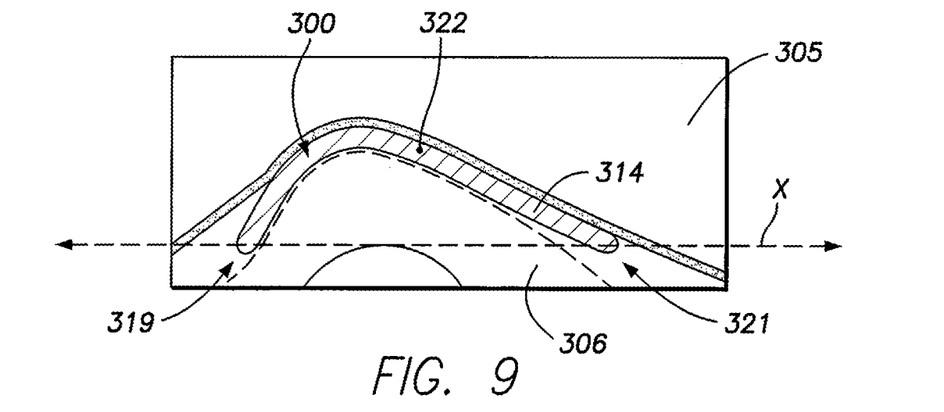
FIG. 9 is another cross-section of a paddle lead formed in accordance with one embodiment that is configured to flex about a central axis when experiencing a fluid pressure from a dura membrane.

FIGS. 7-9 illustrate cross-sections of the paddle lead 300 and, in particular, the different loaded shapes that the paddle lead 300 may have in the epidural space 302. In FIGS. 7-9, the paddle lead 300 is at least partially pressed against the vertebra 305. However, depending on the anatomical structures in the spinal canal of a patient, the paddle lead 300 may also engage other structures, such as the dura membrane.

With respect to FIG. 7, the paddle lead 300 includes a lead body 314 with a central portion 316 and wing portions 318, 320. The wing portions 318, 320 include longitudinal edges 319, 321 of the lead body 314. The lead body 314 also includes an electrode side (or first side) 324 and a posterior side (or second side) 326. The electrode side 324 faces the dura membrane 306, and the posterior side 326 faces the vertebra 305. In some cases, the electrode side 324 may directly engage the dura membrane 306 and/or the posterior side 326 may directly engage the vertebra 305.

A central axis 322 of the paddle lead 300 is indicated and extends through the central portion 316. The central axis 322 extends into and out of the page. The central axis 322 may extend through a geometric center of the cross-section from the proximal end (not shown) to a distal end (not shown) of the lead body 314. Depending on the dimensions of the lead body 314, the central axis 314 may not be perfectly linear. Furthermore, when the paddle lead 300 is in the loaded shape 312, the central axis 322 may not be linear.

As described herein, the paddle lead 300 (or the lead body 314) comprises a flexible material that is configured to flex when a fluid pressure is imposed on the paddle lead 300 in the epidural space 302. The paddle lead 300 is configured to adjust its shape from the pre-loaded shape 310 (FIG. 6) to the loaded-shape 312 shown in FIGS. 7-9. The loaded-shape 312 may be a non-planar contour in which the lead body 314 is folded or curved about the central axis 322. The non-planar contour may be based on the fluid pressure, the dimensions of the epidural space 302, and the dimensions and composition of the paddle lead 300.

FIGS. 7-9 illustrate different non-planar contours of the paddle lead 300 in which the lead body 314 is folded or curved about the central axis 322. It should be noted that FIGS. 7-9 are for illustrative purposes only to demonstrate how the paddle lead 300 permits the fluid pressure within the spinal canal to change a shape of the paddle lead 300. For example, in FIG. 7, the lead body 314 has a substantially uniform radius of curvature along the electrode side 324. In FIG. 8, the lead body 314 has a smaller radius of curvature proximate to the central portion 316 of the lead body 314 and a greater radius of curvature (or more planar shape) along the wing portions 318, 320.

In some embodiments, the central axis 322 may be located proximate to an apex of the loaded lead body 314 as shown in FIGS. 7 and 8. In other embodiments, however, the apex may be located between the central axis 322 and the longitudinal edge 319. FIG. 9 illustrates this configuration. The configuration shown in FIG. 9 may occur due to the shape of an anatomical structure, such as the vertebra 305.

The longitudinal edges 319, 321 extend generally along the central axis 322. As shown in FIGS. 7-9, the longitudinal edges 319, 321 partially close around the dura membrane 306 when the fluid pressure is imposed. In some embodiments, the lead body 314 is configured to flex such that the longitudinal edges 319, 321 move closer to each other within the epidural space 302. More specifically, the width of the lead body 314 in the pre-loaded shape is greater than the width of the lead body 314 in the loaded shape. In some embodiments, the lead body 314 is configured such that the longitudinal edges 319, 321 and the central axis 322 may not exist within a common plane X when the lead body 314 is in the epidural space 302 and the fluid pressure is imposed. For example, as shown in FIG. 9, a plane that extends through the longitudinal edges 319-321 does not include the central axis 322.

FIGS. 10-18 illustrate different mechanisms or methods of delivering a paddle lead to the epidural space. In one or more embodiments, a paddle lead may be configured to be transported from the incision sight and into the epidural space using a delivery tool. Collectively, the paddle lead and the delivery tool may be referred to as a lead-delivery assembly. The delivery tool may direct the paddle lead to a designated location. In some cases, the delivery tool directly engages the paddle lead. For example, the paddle lead may be formed to include a tool receptacle that receives the delivery tool. In other cases, the delivery tool may directly engage another component that is coupled to the paddle lead, such as an insert tray or shroud. The other component may be separate and distinct from the paddle lead. For example, the delivery tool and the other component may be configured to be removed from the body.

Figure 10:
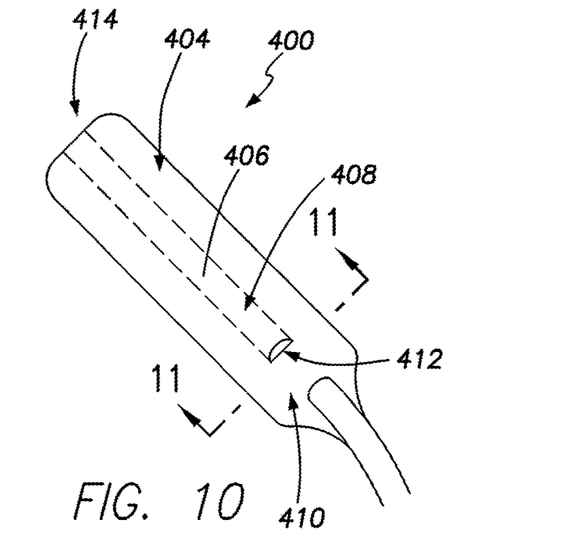
FIG. 10 is an isolated view of a paddle lead having a tool receptacle formed in accordance with one embodiment.
Figure 11:
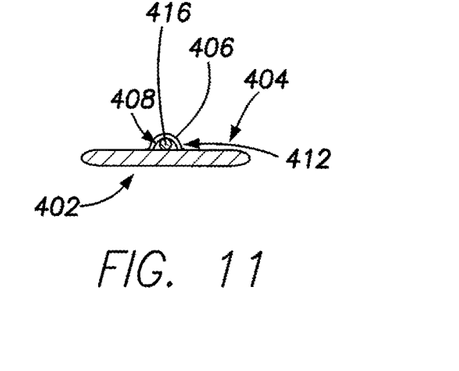
FIG. 11 is a cross-section of the paddle lead of FIG. 10 having a delivery tool located within a receptacle cavity of the paddle lead.

FIGS. 10-16 illustrate embodiments in which the paddle lead includes a tool receptacle that receives the delivery tool. For example, FIGS. 10 and 11 show an isolated view and a cross-section, respectively, of a paddle lead 400. The paddle lead 400 may be similar to the paddle leads 110, 200, 230, and 300 described above. The paddle lead 400 includes an electrode side 402 (FIG. 11) and a posterior side 404. As shown, the posterior side 404 may include a tool receptacle 406 along the posterior side 404. The tool receptacle 406 may comprise a layer of dielectric material that is coupled to and extends along the posterior side 404. The layer of dielectric material may be formed with the paddle lead 400. As such, the tool receptacle 406 may remain with the paddle lead 400 after the paddle lead 400 is positioned in the epidural space. In other embodiments, the tool receptacle 406 may be removed from the paddle lead 400.

As shown, the tool receptacle 406 includes a receptacle cavity 408 that is accessed through the posterior side 404 or through a proximal edge 410 (FIG. 10) of the paddle lead 400. In the illustrated embodiment, the receptacle cavity 408 has a cavity opening 412 that opens along the posterior side 404. In particular embodiments, the receptacle cavity 408 may be a lumina that extends lengthwise from the cavity opening 412 to a distal end 414 of the paddle lead 400.

The receptacle cavity 408 and the cavity opening 412 are configured to receive a delivery tool 416 (FIG. 11). The delivery tool 416 may be an elongated object that is sized and shaped to be inserted through the cavity opening 412 and advanced toward the distal end 414. By way of example, the delivery tool 416 may be a stylet, guidewire, or other elongated object. In some cases, the delivery tool 416 is capable of changing its rigidity. When the delivery tool 416 is inserted into the tool receptacle 406, a leading end of the delivery tool 416 may engage an interior surface and thereby move (e.g., direct) the paddle lead 400. Once the paddle lead 400 is located in the designated location, the delivery tool 416 may be removed.

Figure 12:
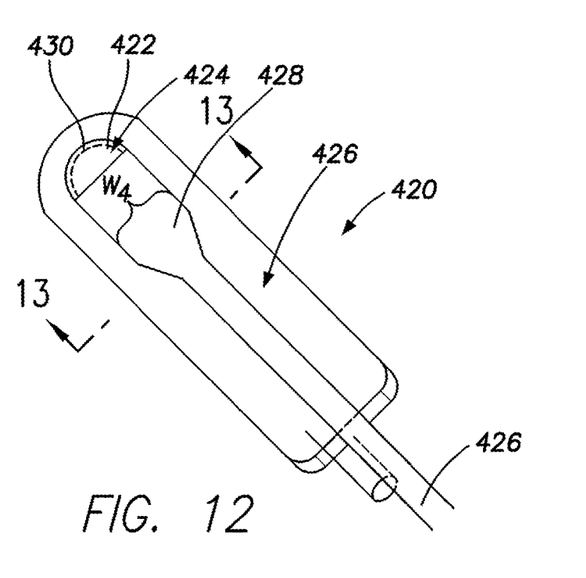
FIG. 12 is a perspective view of a paddle lead having a tool receptacle formed in accordance with one embodiment.
Figure 13:
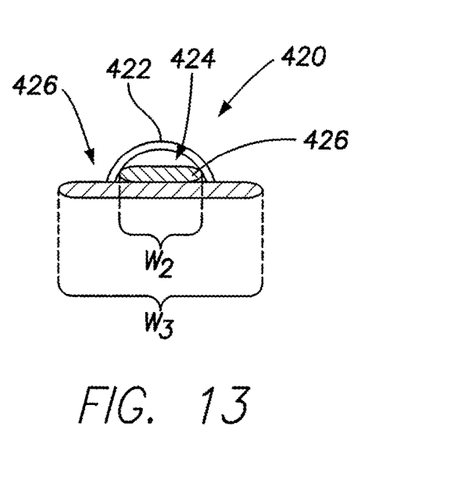
FIG. 13 is a cross-section of the paddle lead of FIG. 12 having a delivery tool located within a receptacle cavity of the paddle lead.

FIG. 12 is a perspective view of a paddle lead 420 having a tool receptacle 422 formed in accordance with one embodiment, and FIG. 13 is a cross-section of the paddle lead 420. In the illustrated embodiment, the tool receptacle 422 is a pocket or shroud having a receptacle cavity 424. The receptacle cavity 424 is accessed along a posterior side 426 of the paddle lead 420. In some embodiments, the pocket 422 and/or the receptacle cavity 424 has a width W2 (FIG. 13) that is configured to extend along a substantial portion of a width W3 of the paddle lead 420. For example, the width $W_2$ may be greater than half of a width $W_3$ of the paddle lead 420. In such embodiments, a delivery tool 426 may also have a width $W_4$ that is substantially equal to the width $W_2$ (e.g., greater than half of the width $W_3$ of the paddle lead 420). More specifically, the delivery tool 426 may have an end portion 428 that extends transverse to the central axis of the paddle lead when the delivery tool 426 is located within the receptacle cavity 424. The end portion 428 of the delivery tool 426 may be spatula-shaped and have a leading edge 430. The leading edge 430 may have the width W4. As such, the delivery tool 426 may provide structural integrity to the paddle lead 420 as the paddle lead 420 is directed into the epidural space. In other words, the delivery tool 426 may function as a stiffening element when the delivery tool 426 is within the pocket 422.

Figure 14:
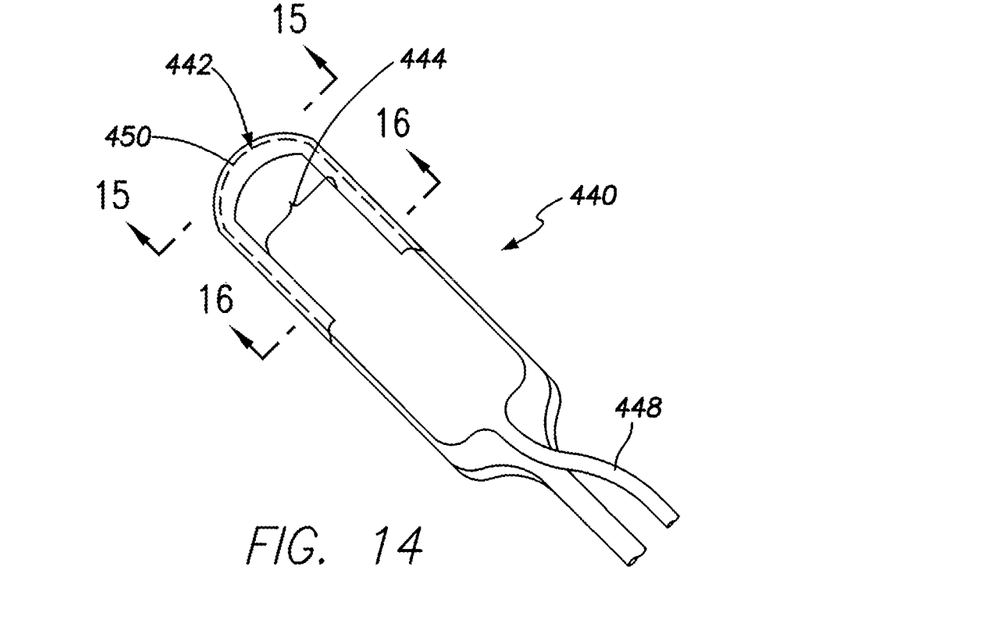
FIG. 14 is a perspective view of a paddle lead having a tool receptacle formed in accordance with one embodiment.
Figure 15:
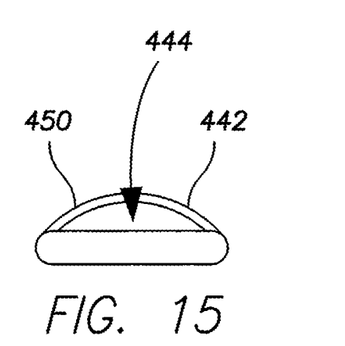
FIG. 15 is a cross-section of the paddle lead of FIG. 14.
Figure 16:
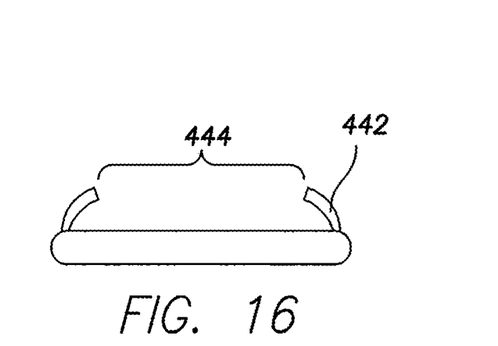
FIG. 16 is another cross-section of the paddle lead of FIG. 14.

FIG. 14 is a perspective view of a paddle lead 440 having a tool receptacle 442 formed in accordance with one embodiment. FIGS. 15 and 16 are cross-sections of the paddle lead 440 taken along the lines 15-15 and 16-16, respectively. The tool receptacle 442 may be similar to the tool receptacle 422 (FIG. 12) and may be referred to as a pocket or shroud. In the illustrated embodiment, the tool receptacle 442 is formed with the lead body of the paddle lead 440. In alternative embodiments, the tool receptacle 442 may be a separate component. For example, the alternative tool receptacle 442 may be like a sleeve that is configured to be removed from the paddle lead 440.

As shown, the tool receptacle 442 includes a receptacle cavity 444 that is configured to receive an end portion 446 of a delivery tool 448. The receptacle cavity 444 is open-sided as shown in FIGS. 14 and 16 for a majority of a length of the paddle lead 440. However, the tool receptacle 442 may have a pocket end 450 that receives a distal end of the delivery tool 448. The delivery tool 448 may be dimensioned to extend across a majority or an entirety of a width of the receptacle cavity 444.

Figure 17:
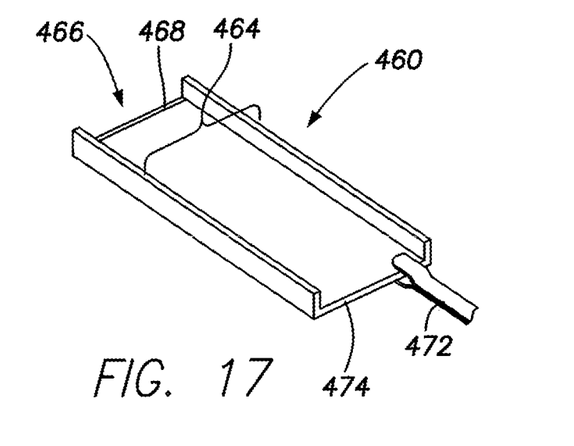
FIG. 17 is a perspective view of an insert tray formed in accordance with one embodiment that is configured to receive a paddle lead.
Figure 18:
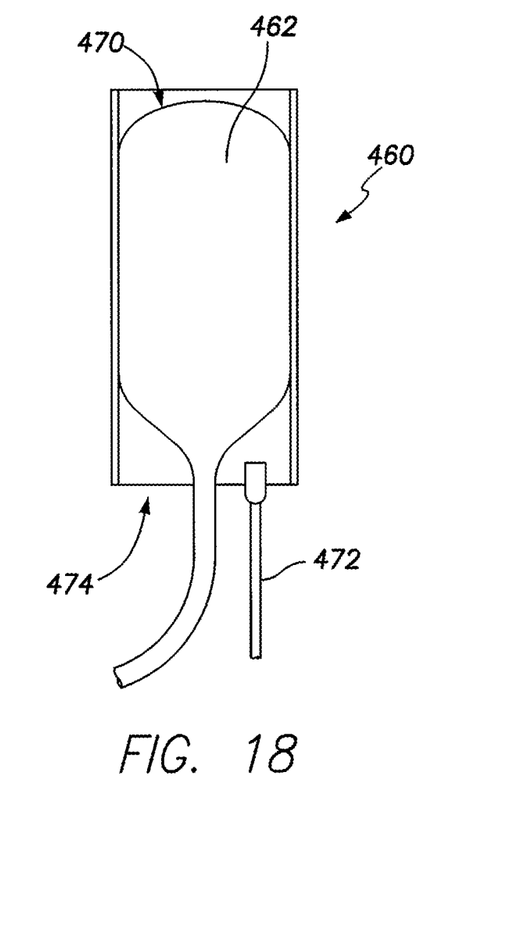
FIG. 18 is a plan view of the insert tray of FIG. 17 holding the paddle lead.

FIG. 17 is an isolated perspective view of an insert tray 460, and FIG. 18 is a plan view of the insert tray 460 holding a paddle lead 462. The insert tray 460 has an open-sided recess 464 that is sized and shaped to receive the paddle lead 462. The insert tray 460 may have a distal end 466 that includes a lip 468. The lip 468 may protect a distal end 470 of the paddle lead 462 to facilitate the insertion process. The lip 468 may also prevent inadvertent sliding of the paddle lead 462 in the insertion direction. During the insertion process, a delivery tool 472 may engage a portion of the insert tray 460 to direct the insert tray 460 into the body. For example, the delivery tool 472 may have a clip that grips a proximal end 474 of the insert tray 460.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "central," "upper," "lower," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

Although the invention has been described with reference to certain embodiments, persons skilled in the art will recognize that changes may be made in form and detail without departing from the spirit and scope of the invention.

The following claims recite aspects of certain embodiments of the inventive subject matter and are considered to be part of the above disclosure.

What is claimed is:

1. A neurostimulation paddle lead comprising:
a lead body that includes first and second wing portions joined by a central portion, the first and second wing portions and the central portion being elongated between a distal end and a proximal end, a central axis extending along a length of the lead body, the lead body including opposite first and second sides that extend between the distal and proximal ends, the first and second wing portions including longitudinal edges that extend along the length of the lead body in a common direction as the central axis;
wherein the lead body comprises a flexible material that is configured to flex when a fluid pressure in a dura space is imposed on the second side of the lead body by a spinal fluid, the lead body configured to form a non-planar contour that folds or curves about the central axis to maintain the first side against a dural membrane in response to the fluid pressure imposed on the second side, wherein the lead body is to flex and conform to the dural membrane when the second side of the lead body experiences a designated amount of the fluid pressure between 5 cmH2O and 20 cmH2O;
electrodes disposed along the first side of the lead body and configured to apply a neurostimulation therapy within an epidural space of a patient, the electrodes being electrically coupled to conductive pathways that extend through the proximal end of the lead body, wherein the first side is configured to engage the dural membrane and the second side is configured to be exposed to the spinal fluid;
an edge structure provided along the longitudinal edges of the lead body, the edge structure made of a material that is more rigid that the flexible material forming the lead body; and
wherein the edge structure includes a rigid dielectric material that extends along the longitudinal edges for at least a portion of the length, the dielectric material to electrically insulate the electrodes along the longitudinal edges of the lead body when applying the neurostimulation therapy.

2. The paddle lead of claim 1, wherein the distal end includes an end structure made of a material that is more rigid that the flexible material forming the lead body.

3. The paddle lead of claim 1, wherein, as an operative shape of the lead body changes, an effective arrangement of the electrodes changes with respect to each other.

4. The paddle lead of claim 3, wherein at least one of a pattern or arrangement of the electrodes is re configured or re-arranged based on the operative shape of the lead body.

5. The paddle lead of claim 4, wherein at least some of an array or pattern of the electrodes is irregular, such that at least one row or column of the electrodes has different separation distances between adjacent electrodes and at least one of adjacent rows or columns have different separation distances between the adjacent electrodes.

6. The paddle lead of claim 1, wherein the lead body includes a width that extends transverse to the central axis between the longitudinal edges, the lead body further including a thickness that extends between the first and second sides, the thickness varying such that the central portion has a greater thickness relative to a thickness of at least one of the first and second wing portions.

7. The paddle lead of claim 6 wherein the thickness varies gradually as the thickness extends along at least one of the width or length.

8. The paddle lead of claim 6 wherein the thickness reduces or tapers as the first and second wing portions approach the corresponding longitudinal edges.

9. The paddle lead of claim 6, wherein the first and second sides represent an electrode side and a posterior side, respectively, the posterior side of the central portion including a tool receptacle configured to receive a tool, the tool receptacle extending along the central axis of the central portion in a region of the central portion having the greater thickness relative to the thickness of at least one of the first and second wing portions.

10. The paddle lead of claim 9, wherein the tool receptacle comprises a layer of dielectric material that is coupled to and extends along the posterior side, the layer of dielectric material formed with the lead body such that the tool receptacle remains with the lead body after the paddle lead is positioned in the epidural space.

11. The paddle lead of claim 1, wherein the first and second sides represent an electrode side and a posterior side, respectively, the posterior side of the central portion including a tool receptacle configured to receive a tool, the tool receptacle extending the length of the lead body proximate to at least one of the first and second wing portions or the central portion.

12. The paddle lead of claim 1, wherein the flexible material is homogenously formed from a common material, from the first side to the second side of the lead body, throughout the first and second wing portions and the central portion.

* * * * *